United States Patent
Tsurumoto et al.

(10) Patent No.: US 8,758,244 B2
(45) Date of Patent: Jun. 24, 2014

(54) INFORMATION PROCESSING SYSTEM AND INFORMATION PROCESSING APPARATUS

(75) Inventors: Takashi Tsurumoto, Saitama (JP); Masahiro Nakano, Tokyo (JP); Shiro Omori, Kanagawa (JP); Kazumoto Kondo, Kanagawa (JP); Tatsushi Banba, Tokyo (JP)

(73) Assignee: Sony Corporation (JP)

( * ) Notice: Subject to any disclaimer, the term of this patent is extended or adjusted under 35 U.S.C. 154(b) by 354 days.

(21) Appl. No.: 13/159,538

(22) Filed: Jun. 14, 2011

(65) Prior Publication Data

US 2011/0319725 A1 Dec. 29, 2011

(30) Foreign Application Priority Data

Jun. 25, 2010 (JP) ................ P2010-145425

(51) Int. Cl.
*A61B 5/00* (2006.01)
*G08B 21/04* (2006.01)

(52) U.S. Cl.
CPC ............ *G08B 21/04* (2013.01); *G08B 21/0469* (2013.01); *G08B 21/0453* (2013.01)
USPC ........................................................ 600/301

(58) Field of Classification Search
USPC ................................................. 600/300–301
See application file for complete search history.

(56) References Cited

U.S. PATENT DOCUMENTS

| | | | | |
|---|---|---|---|---|
| 7,724,147 B2 * | 5/2010 | Brown | ...................... | 340/573.1 |
| 7,979,284 B2 * | 7/2011 | Brown | .............................. | 705/2 |
| 2002/0062069 A1 * | 5/2002 | Mault | ........................... | 600/300 |
| 2002/0107433 A1 * | 8/2002 | Mault | ........................... | 600/300 |
| 2002/0186243 A1 * | 12/2002 | Ellis et al. | ..................... | 345/753 |
| 2003/0025604 A1 * | 2/2003 | Freeman | ..................... | 340/573.1 |
| 2004/0133453 A1 * | 7/2004 | Jomini et al. | ..................... | 705/2 |
| 2004/0249250 A1 * | 12/2004 | McGee et al. | ............... | 600/300 |
| 2005/0171410 A1 * | 8/2005 | Hjelt et al. | .................... | 600/300 |
| 2006/0026316 A1 * | 2/2006 | Milenkovic et al. | ............ | 710/62 |
| 2006/0074279 A1 * | 4/2006 | Brover | ..................... | 600/300 |
| 2007/0016448 A1 * | 1/2007 | Brown | ............................. | 705/2 |
| 2007/0037614 A1 * | 2/2007 | Rosenberg | ................ | 455/575.1 |
| 2007/0124179 A1 * | 5/2007 | Brown | ............................. | 705/3 |
| 2008/0154099 A1 * | 6/2008 | Aspel et al. | .................... | 600/301 |
| 2008/0228045 A1 * | 9/2008 | Gao et al. | ...................... | 600/301 |
| 2009/0093688 A1 * | 4/2009 | Mathur | ........................ | 600/300 |
| 2009/0281392 A1 * | 11/2009 | Brown | .......................... | 600/300 |
| 2009/0281393 A1 * | 11/2009 | Smith | ............................ | 600/301 |
| 2010/0016683 A1 * | 1/2010 | Lemmers et al. | ............. | 600/301 |
| 2010/0107195 A1 * | 4/2010 | Hsu et al. | ........................ | 725/44 |
| 2010/0125182 A1 * | 5/2010 | Schroeter et al. | ............. | 600/301 |
| 2010/0154006 A1 * | 6/2010 | Reams | ............................ | 725/58 |
| 2010/0164731 A1 * | 7/2010 | Xie | ............................. | 340/573.1 |

(Continued)

FOREIGN PATENT DOCUMENTS

JP 2006-246230 A 9/2006

*Primary Examiner* — Bill Thomson
*Assistant Examiner* — Bobby Soriano
(74) *Attorney, Agent, or Firm* — Lerner, David, Littenberg, Krumholz & Mentlik, LLP

(57) ABSTRACT

An information processing system includes: a physical measurement apparatus measuring the body of a user and radio-transmitting measurement data; and an information processing apparatus receiving the measurement data radio-transmitted from the physical measurement apparatus, displaying information on the measurement data of the user on a screen, and displaying a notice prompting the user to conduct measurement when no measurement data is received by a predetermined time for measurement.

14 Claims, 12 Drawing Sheets

(56) References Cited

U.S. PATENT DOCUMENTS

| | | | |
|---|---|---|---|
| 2010/0212675 A1* | 8/2010 | Walling et al. | 128/898 |
| 2010/0222046 A1* | 9/2010 | Cumming | 455/418 |
| 2010/0283601 A1* | 11/2010 | Tai et al. | 340/539.12 |
| 2011/0124996 A1* | 5/2011 | Reinke et al. | 600/365 |
| 2011/0184247 A1* | 7/2011 | Contant et al. | 600/300 |
| 2012/0041917 A1* | 2/2012 | Newton et al. | 706/46 |

* cited by examiner

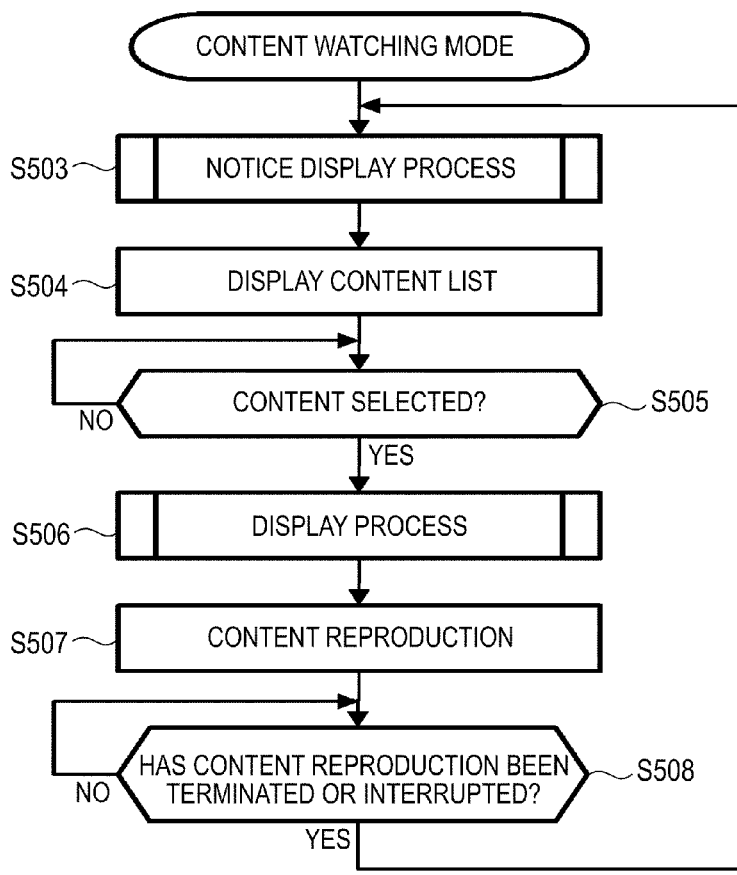
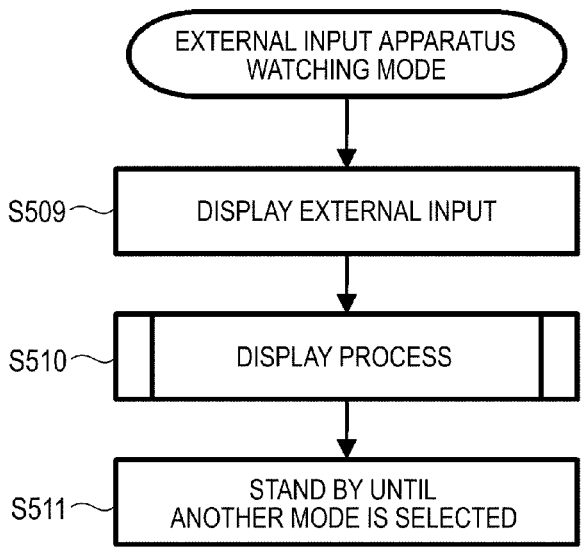

INFORMATION PROCESSING SYSTEM AND INFORMATION PROCESSING APPARATUS

CROSS-REFERENCE TO RELATED APPLICATION

The present application claims priority from Japanese Patent Application No. JP 2010-145425 filed in the Japanese Patent Office on Jun. 25, 2010, the entire content of which is incorporated herein by reference.

FIELD OF THE INVENTION

The present disclosure contains subject matter related to that disclosed in Japanese Priority Patent Application JP 2010-145425 filed in the Japan Patent Office on Jun. 25, 2010, the entire contents of which are hereby incorporated by reference.

BACKGROUND OF THE INVENTION

Presently, people are highly health-conscious, and physical measurement apparatus such as scales, blood pressure monitors, body composition meters, and passometers are widely used not only in medical institutions but also in homes. In order to control physical conditions properly, it is preferable for each person to check daily changes in physical conditions by him- or herself by conducting measurement using those physical measurement apparatus on a daily basis.

For example, a health care program has been proposed, which includes the steps of transmitting measurement data obtained by a user by measuring his or her weight using a scale to a television or a different type of digital apparatus every day, storing the received measurement data at the television with the date and time of measurement, and displaying the data in the form of a graph on a display screen when the user wishes to see it (see JP-A-2006-246230 (Patent Document 1)). The user can check changes in information concerning his or her physical condition such as the weight from the graph displayed on the screen. Further, the user may be motivated by checking the graph to continue the measurement the next day and afterwards.

Instead of wired communication such as wired USB, radio communication utilizing a wireless network or the like may be conveniently used as means for communication between the physical measurement apparatus and the digital apparatus. For example, Continua standard that is a radio communications standard for health-care apparatus has been formulated by Continua Health Alliance which is promoting standardization of connection compatibility between physical measurement apparatus and digital apparatus.

Instead of recording measurement data using a household digital apparatus such as a television, the data may be sent to an external server through a network such as the internet to have the data managed by the server. A user can look at daily measurement data in the form of a graph by accessing the server from the household digital apparatus such as a television.

In order to control one's physical condition properly, it is important to conduct measurement using a physical measurement apparatus every day. However, most users of physical measurement apparatus tend to neglect the measurement sometimes, whereas the users watch television programs substantially every day as if it were a daily routine. A wide variety of television programs showing news, sports, dramas, talk shows, etc. are broadcast every day. Watching television is a fun, and a television can be easily turned on through a substantially unconscious action of a user. On the contrary, a physical measurement apparatus is used for only one purpose, i.e., the measurement of physical conditions, and measuring activities themselves are not attractive. When a user forgets to conduct measurement, it is difficult for the user to remember the task unless urged by someone.

SUMMARY OF THE INVENTION

It is desirable to provide an information processing system which includes a physical measurement apparatus such as a scale, a blood pressure monitor, a body composition meter, or a passometer and a digital apparatus such as a television receiving measurement data from the physical measurement apparatus and displaying daily measurement data in the form of a graph or the like in a preferable manner. It is also desirable to provide an information processing apparatus of such a system.

It is also desirable to provide an information processing system and an information processing apparatus which allow daily measurement data to be displayed in the form of a graph or the like in a preferable manner while preventing a user from carelessly neglecting measurement using a physical measurement apparatus.

(1) An embodiment of the present disclosure is directed to an information processing system including a physical measurement apparatus measuring the body of a user and radio-transmitting measurement data, and an information processing apparatus receiving the measurement data radio-transmitted from the physical measurement apparatus, displaying information on the measurement data of the user on a screen, and displaying a notice prompting the user to conduct measurement when no measurement data is received by a predetermined time for measurement.

The term system in this context means a logical collection of a plurality of apparatus for functional modules for implementing particular functions), and the term is used regardless of whether the apparatus or functional modules are contained in a single housing or not.

(2) Another embodiment of the present disclosure is directed to an information processing apparatus including a display section, a radio communication section, and a storage section. The radio communication section receives measurement data of a user radio-transmitted from a physical measurement apparatus. The display section displays information on the measurement data from the user. A notice prompting the user to conduct measurement is displayed when no measurement data is received by a predetermined time for measurement.

(3) According to still another embodiment of the present disclosure, the information processing apparatus may be configured to further include an audio output section to provide audio output of an alarm sound prompting the user to conduct measurement when no measurement data is received by the time for measurement.

(4) According to yet another embodiment of the present disclosure, the information processing apparatus may be configured such that measurement data of each user received from the physical measurement apparatus is stored in the storage section in association with a time and date for measurement for each user. Changes in the measurement data of the user may be displayed at the display section in the form of a graph.

(5) According to still yet another embodiment of the present disclosure, the information processing apparatus may be configured such that the measurement data is transmitted from the physical measurement apparatus, the data being accompanied by identification information of the user. A notice may be displayed at the display section when the received data are significantly different from past measurement data of the same user which have been stored in the storage section to notify the user of the difference.

(6) According to further another embodiment of the present disclosure, the information processing apparatus may be configured to further include a plurality of physical measurement apparatus. A separate time for measurement may be set for each of the physical measurement apparatus when measurement data of a user are received from the plurality of physical measurement apparatus. A process of displaying a notice prompting the user to conduct measurement may be performed for each of the physical measurement apparatus.

(7) According to still further another embodiment of the present disclosure, the information processing apparatus may be configured such that the time for measurement is determined based on the date and time of past measurement data.

(8) According to yet further another embodiment of the present disclosure, the information processing apparatus may be a television receiver including an antenna, a tuner circuit for selecting a desired channel from broadcast waves received by the antenna, a demultiplexer extracting a video signal and an audio signal from a stream transmitted over the selected channel, a video signal processing circuit processing the video signal, an audio processing circuit processing the audio signal, and an audio output section. The apparatus may display the processed video signal at the display section and may provide audio output of the processed audio signal from the audio output section.

(9) According to still yet further another embodiment of the present disclosure, the information processing apparatus may be configured such that determination is made on whether the measurement data of the user have been received by the time for measurement or not, when the power supply of the apparatus is turned on. A notice prompting the user to conduct measurement may be displayed at the display section depending on the result of the determination.

(10) According to a further embodiment of the present disclosure, the information processing apparatus may be configured such that the determination on whether the measurement data of the user have been received by the time for measurement or not is made at a time which precedes the ending time of a program of the selected channel by a predetermined length of time. A notice prompting the user to conduct measurement may be displayed at the display section depending on the result of the determination.

(11) According to a still further embodiment of the present disclosure, the information processing apparatus may be configured such that the determination on whether the measurement data of the user have been received by the time for measurement or not is made immediately after the user performs a channel switching operation. A notice prompting the user to conduct measurement may be displayed at the display section depending on the result of the determination.

(12) According a yet further embodiment of the present disclosure, the information processing apparatus may be configured to further include means for recording received content and means for reproducing the recorded content. The determination on whether the measurement data of the user have been received by the time for measurement or not may be made when an item to be reproduced is selected from the recorded content. A notice prompting the user to conduct measurement may be displayed at the display section depending on the result of the determination.

(13) According to a still yet further embodiment of the present disclosure, the information processing apparatus may be configured to further include means for inputting content from outside and means for reproducing the content input from outside. The determination on whether the measurement data of the user have been received by the time for measurement or not may be made during the reproduction of the content input from outside. A notice prompting the user to conduct measurement may be displayed at the display section depending on the result of the determination.

(14) According a furthermore embodiment of the present disclosure, the information processing apparatus may be configured such that the determination on whether the measurement data of the user have been received by the time for measurement or not is made when the user performs a predetermined operation. A notice prompting the user to conduct measurement may be displayed at the display section depending on the result of the determination.

(15) According to a still furthermore embodiment of the present disclosure, the information processing apparatus may be configured such that the determination on whether the measurement data of the user have been received by the time for measurement or not is made when an operation of turning off the power supply is performed. A notice prompting the user to conduct measurement may be displayed at the display section depending on the result of the determination.

(16) According to a yet furthermore embodiment of the present disclosure, the information processing apparatus may be configured to further include a human sensor. The determination on whether the measurement data of the user have been received by the time for measurement or not may be made when the user is detected based on a sensor output from the human sensor. A notice prompting the user to conduct measurement may be displayed at the display section depending on the result of the determination.

According to the embodiments of the present disclosure, daily measurement data can be displayed without missing days in a preferable manner in the form of a graph or the like while preventing a user from carelessly neglecting measurement using a physical measurement apparatus.

According to the above items (1) to (16), when periodic transmission of measurement data from a physical measurement apparatus to the television receiver is missed, a notice prompting the user to conduct measurement is displayed on the screen of the television receiver at appropriate timing. Thus, daily measurement data can be displayed without missing days in a preferable manner in the form of a graph or the like while preventing a user from carelessly neglecting measurement.

According to the item 8, the information processing apparatus may be a television receiver. According to the items 9 to 16, a notice prompting a user to conduct measurement can be displayed at such timing that disturbance to a television program being watched is minimized.

Other objects, features and advantages of the present disclosure will be apparent from the detailed description with reference to embodiments described later and the attached drawings.

BRIEF DESCRIPTION OF THE DRAWINGS

FIG. 5D is a flow chart showing operational steps executed at the television receiver 10 in a content watching mode;

FIG. 5E is a flow chart showing operational steps executed at the television receiver 10 in an external input apparatus watching mode;

DETAILED DESCRIPTION OF THE INVENTION

An embodiment of the present disclosure will now be described with reference to the drawings.

Figure 10:
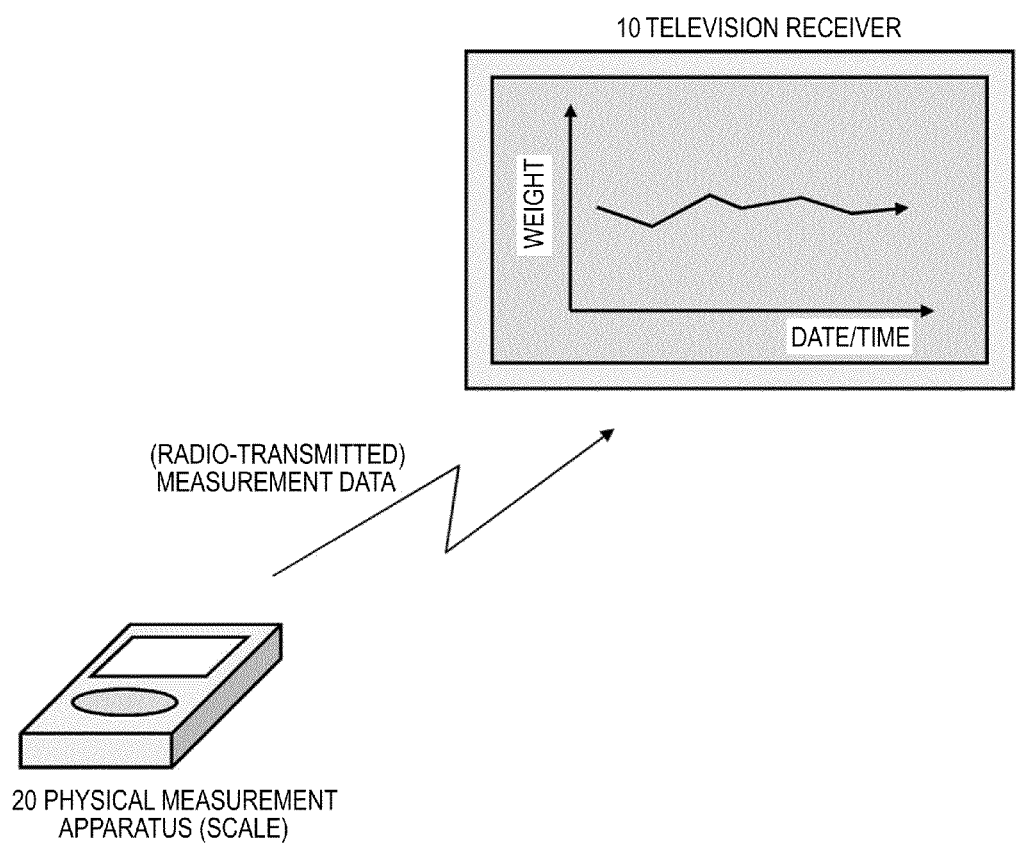
FIG. 10 is an illustration of an exemplary configuration of an information processing system according to an embodiment of the present disclosure.

As shown in FIG. 10, an information processing system according to an embodiment of the present disclosure includes a physical measurement apparatus 20 such as a scale, a blood pressure monitor, a body composition meter, or a passometer and a television receiver (or a different type of digital apparatus) 10 which receives measurement data from the physical measurement apparatus 20 and displays daily measurement data in the form of a graph or the like. For example, when a user measures his or her weight using a scale every day, resultant measurement data are radio-transmitted to the television receiver 10. The received measurement data are stored at the television receiver 10 with dates and times of measurement, and the data are displayed on a display screen in the form of a graph when the user desires.

Figure 11:
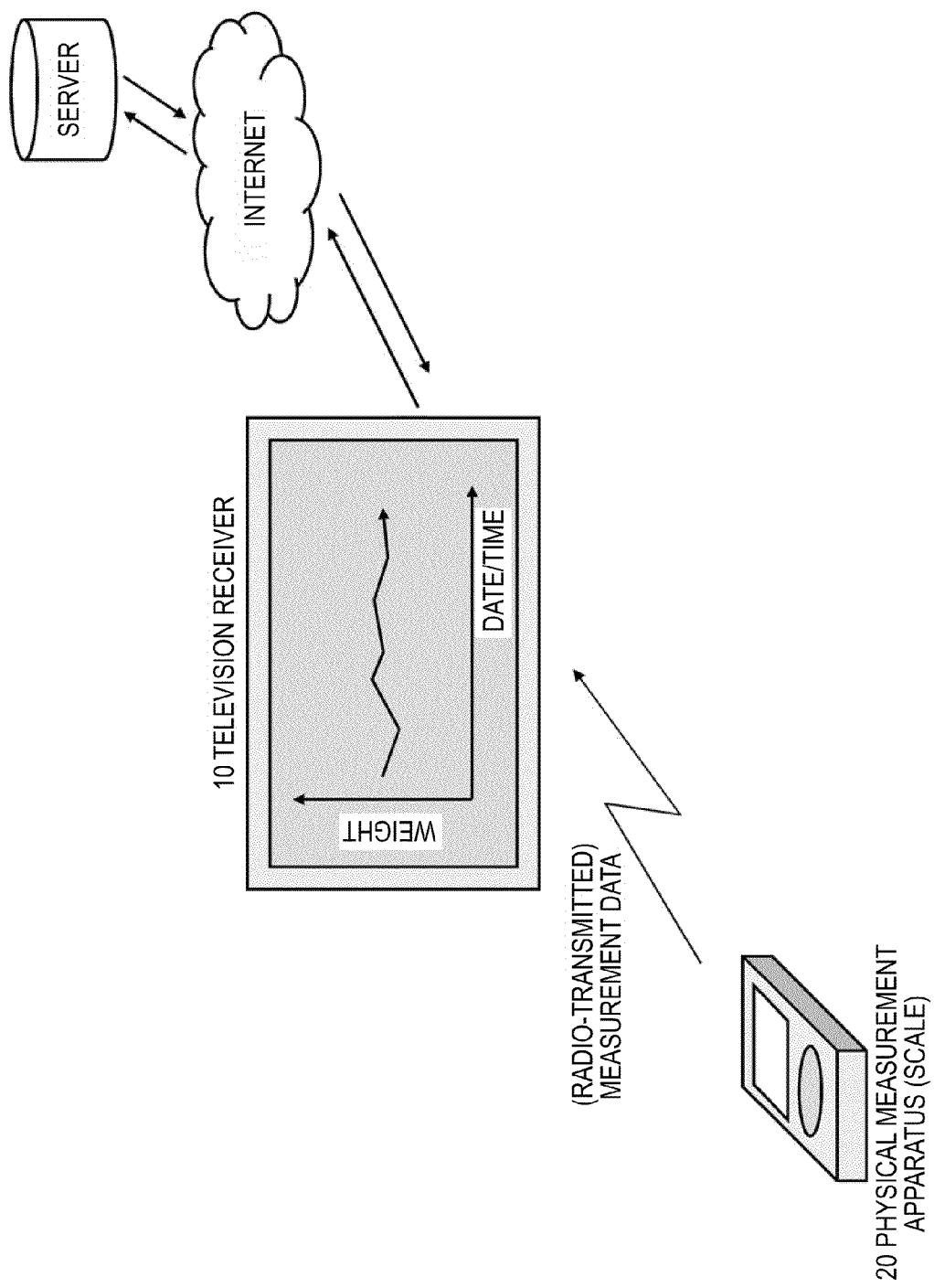
FIG. 11 is an illustration of a modification of the information processing system shown in FIG. 10.

As a modification to the information processing system shown in FIG. 10, instead of storing the measurement data at the television receiver 10, the data may be transmitted to an external server through a network such as the internet to have the data managed by the server, as shown in FIG. 11. The user can look at the daily measurement data in the form of a graph by accessing the server from the television receiver 10.

In the information processing system shown in FIGS. 10 and 11, possible destinations of the measurement data transmitted from the physical measurement apparatus 20 other than the television receiver 10 include digital apparatus such as personal computers. It is considered advantageous to transmit measurement data to the television receiver 10 because the television receiver 10 is a type of household apparatus which have spread at a higher prevalence compared to other types of digital apparatus having a display screen and which are used for a long time and are therefore available for receiving measurement data substantially any time of a day. On the contrary, the operable time of the system is limited when a personal computer is used because it is not easy to allow reception of measurement data at the PC when the PC is in a power-off state (or standby state). Further, it is not easy to operate a personal computer for aged people who have higher needs for physical measurement. When a dedicated box is provided for receiving measurement data, the cost of the system will increase. When measurement data are transmitted to a mobile phone instead of the television receiver 10, the system is less likely to operate with stability because the mobile phone is not always located in a fixed position and there is also a possibility of a dead battery.

Figure 1:
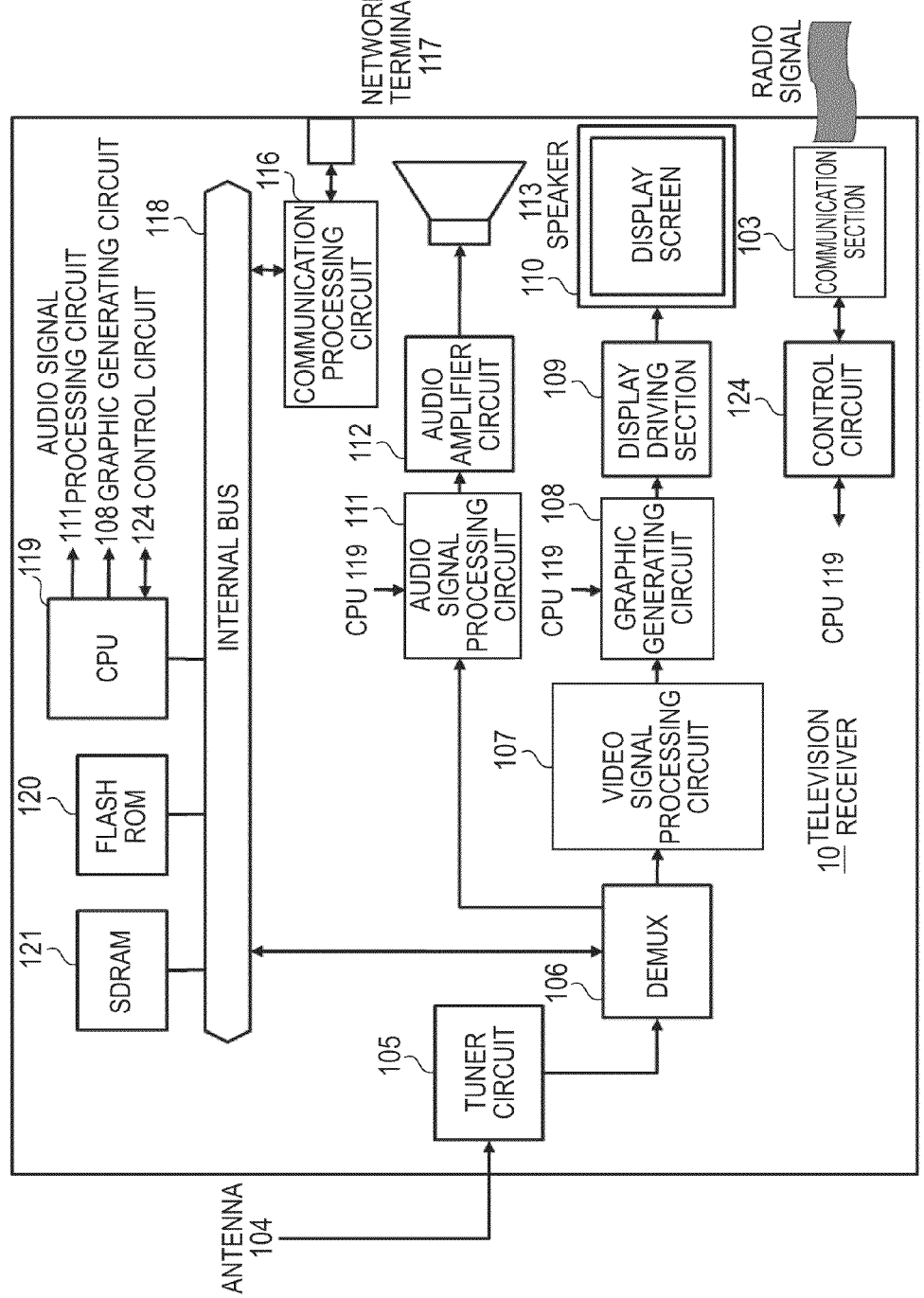
FIG. 1 is a schematic diagram showing an exemplary configuration of a television receiver 10.

FIG. 1 schematically shows an exemplary configuration of the television receiver 10 used in the information processing system shown in FIG. 10 or 11.

Digital broadcast waves for broadcasting television programs can be received by an antenna 104. A tuner circuit 105 selects a stream of a desired channel (tuning) when the digital broadcast waves are input to the same from the antenna 104. A demultiplexer ((DEMUR) 106 extracts video signals, audio signals, and data broadcast signals from the stream selected by the tuner circuit 105. The data broadcast signals include information such as an EPG (electronic program guide).

The video signals are input to a video signal processing circuit 107 in which the signals receive required signal processing. Thereafter, on-screen message information generated by a graphics generating circuit 108 is superimposed on the signals as occasion demands, and the signals are output by a display driving section 109 to a display screen 110 and displayed on the same. For example, the graphics generating section 109 generates an image prompting a user to conduct measurement using the physical measurement apparatus 20 as an image to serve as an on-screen image message according to an instruction from a CPU 119 which will be described later.

The audio signals are input to an audio signal processing circuit 111 in which the signals receive required signal processing. Thereafter, the signals are amplified to a desired audio level by an audio amplifier circuit 112, and the signals drive a speaker 113. The audio signal processing circuit 111 performs audio synthesis to produce an alarm sound or the like for prompting the user to conduct measurement using the physical measurement apparatus 20.

A communication section 103 of a wireless network transmits and receives radio signals to and from the physical measurement apparatus 20 such as a scale. A control circuit 124 controls communication operations of the communication section 103. Specifically, the control circuit 124 controls a communication operation for transmitting transmission data required by a high-order application layer executed on the CPU 119 which will be described later. The circuit 124 decodes signals received through the communication section 130 and supplies the signals to the high-order application layer.

In the example shown in FIG. 1, the television receiver 10 is controlled with a remote controller using a radio wave communication system, and the communication section 103 is used for control with a remote controller. A user controls the television receiver 10 using a remote controller (not shown), and a radio-transmitted control code is received at the communication section 103.

The television receiver 10 is connected to an external network such as the internet through a network terminal 117. A communication process circuit 116 is constituted by an Ethernet (registered trademark) interface, and the circuit performs communication processes over the external network according to instructions from the CPU 119 which will be described later.

Circuit components such as a CPU 119, a flash ROM 120, and a DRAM 121 are provided for controlling the television receiver 10 as a whole. Control codes received by a remote control receiver 122 (or the communication section 103) are transferred to the CPU 119 through an internal bus 118. The CPU 119 decodes the control codes to control operations of the television receiver 10. Information received at the communication section 103 is input to the CPU 119 through the control circuit 124.

For example, the CPU 119 stores measurement data of each user received from the physical measurement apparatus 20 in the flash ROM 120 or another storage device, each piece of measurement data being associated with the time and date of measurement.

The CPU 119 instructs the graphics generating circuit 108 to collect measurement data of each user, to create a graph from the data, and to display the graph on the screen. Alternatively, the CPU 119 may instruct the communication processing circuit 116 to transmit measurement data of each user received from the physical measurement apparatus 20 to a predetermined server on the external network and may instruct the circuit 116 to access measurement data of a user saved in the server or the data of a graph obtained by collecting the measurement data.

The CPU 119 instructs the graphics generating circuit 108 to generate an on-screen message for prompting a user to conduct measurement using the physical measurement apparatus 20 and instructs the audio signal processing circuit 111 to perform audio synthesis to generate an alarm sound for prompting a user to conduct measurement.

Figure 2:
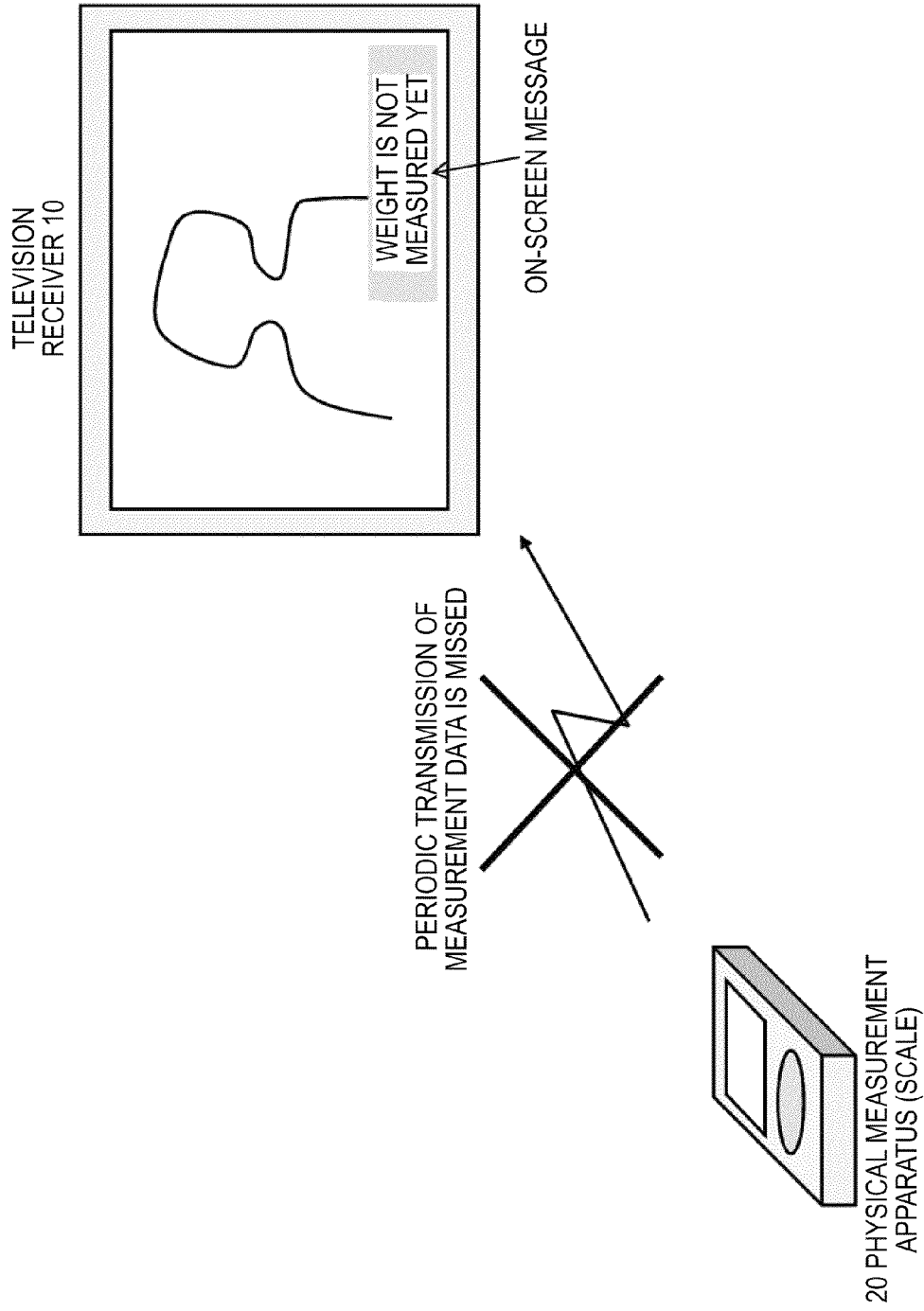
FIG. 2 is an illustration showing how an on-screen message for prompting a user to measure the weight is displayed on a screen of the television receiver 10.

For example, when no measurement data is transmitted from the physical measurement apparatus 20 past a certain time of the day, i.e., a time set by a user in advance as a time for daily measurement or a time at which the user usually conducts measurement, an on message prompting the user to conduct measurement of his or her weight or the like is displayed over the presently viewed program on the screen of the television receiver 10 as shown in FIG. 2. The user may be prompted to measurement not only by an on-screen message but also by an alarm sound. In particular, words generated using audio synthesis will be more clearly understood. While an on-screen message cannot be displayed while the power supply of the television receiver 10 is off, the use of an alarm sound or words generated by audio synthesis allows the user to be prompted to measurement only by an operation of the audio output section of the television receiver. A time of the day set by a user as time to conduct measurement using the physical measurement apparatus 20 will be hereinafter referred to as "time for measurement". A time for measurement may be also understood as a time for prompting a user to conduct measurement. A plurality of times of the day may be set as times for measurement. A method of determining a time for measurement will be described later.

It has been stated above that the communication section 103 serves both of the wireless network for connecting the television receiver to the physical measurement apparatus 20 and operations using a remote controller. For example, radio communication methods of this type applicable to the embodiment include the ZigBee method which has been standardized as the short-range radio communication standard RF4CE (Radio Frequency for Consumer Electronics) or IEEE 802.15.4 standard.

Presently, remote controllers utilizing electric waves instead of infrared light are available, and some of such remote controllers utilize the RF4CE method. The RF4CE method is used in this embodiment for the following reasons. The battery of a remote controller can operate over a long life. Power consumption can be kept low even when a receiver of the communication section 103 is normally kept in a receive mode. A sufficient control distance can be obtained. While other types of radio format such as the Bluetooth format may be used by the communication section 103, the use of the RF4CE method provides advantages listed below.

(1) Power consumption of a transmitter can be substantially kept zero when the transmitter is not transmitting or in a standby state, and power required for one transmission operation can be kept small. Therefore, even when a transmitter is provided in the physical measurement apparatus 20, the transmitter can be driven by a dry cell. There is no need for a power switch, and the life of the battery can be kept long. It is therefore possible to provide a scale which is similar to scales according to the related art in user friendliness.

(2) The power consumption of a receiver can be very small even when it is kept ready for reception, and the television receiver 10 can receive data even in the standby state like the remote controller. Therefore, a user is not required to turn on the power supply of the television receiver 10 to start measurement.

(3) One receiver can be used for reception of signals from both of an RF remote controller and a measurement apparatus, and the receiver can receive data from a plurality of physical measurement apparatus, which is advantageous in terms of cost.

(4) Transmitted data can be enciphered. Therefore, the data will not be easily accessed even if the communication is bugged.

As will be described later, a human sensor such as an infrared human sensor or a camera may be incorporated in the television receiver 10. The illustration of such a human sensor is omitted FIG. 1.

Figure 3:
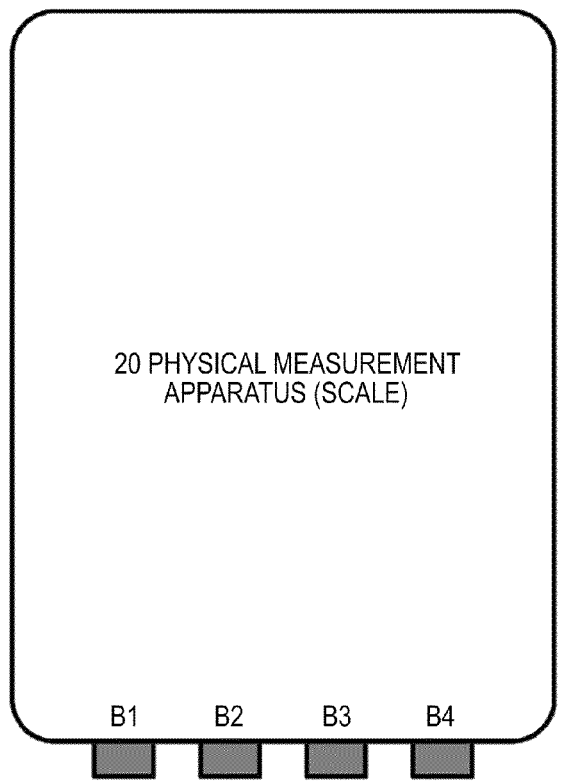
FIG. 3 is an illustration schematically showing an external configuration of a physical measurement apparatus 20.
Figure 4:
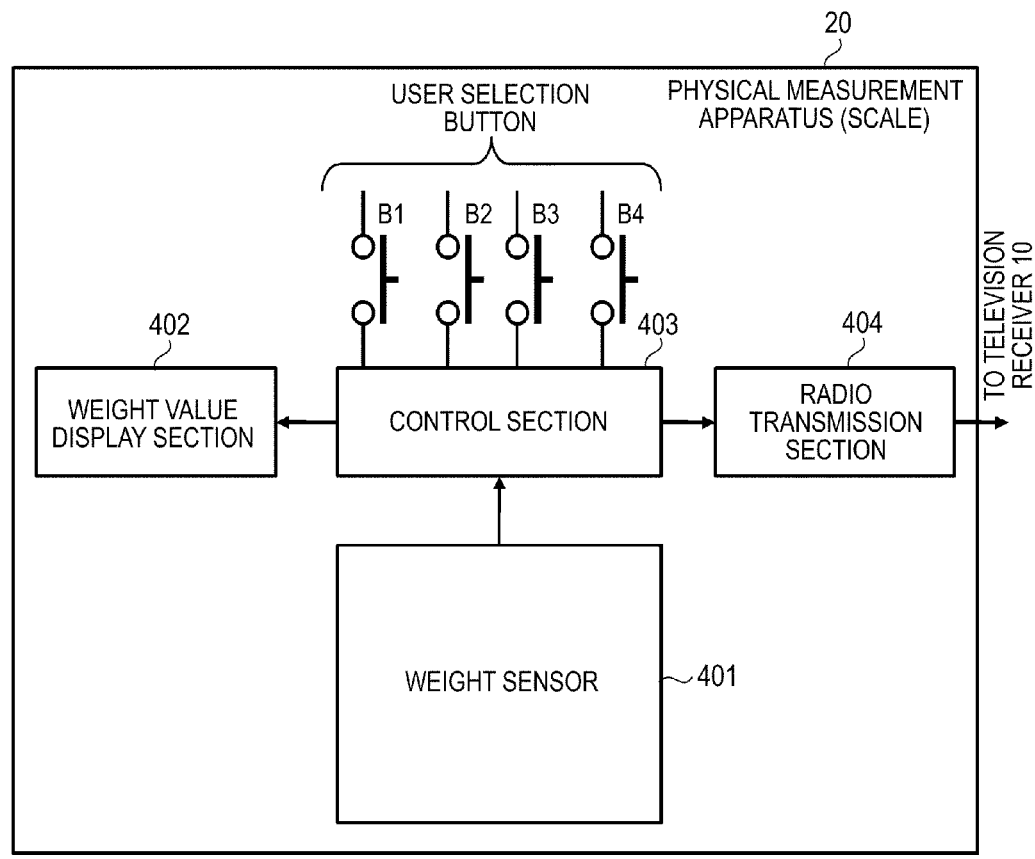
FIG. 4 is a diagram showing an exemplary internal configuration of the physical measurement apparatus 20.

FIG. 3 schematically shows an external configuration of the physical measurement apparatus 20 used in the information processing system shown in FIG. 10 or 11. FIG. 4 shows an exemplary internal configuration of the physical measurement apparatus 20. The illustrated physical measurement apparatus 20 is a scale having a body fat measuring function, and scale includes user selection buttons B1 to B4 for identifying a person to be measured.

Any of numbers 1 to 4 is assigned to each user or each family member in advance. A user conducts measurement using the physical measurement apparatus 20 after pressing the user selection button associated with the number assigned to the user. The weight of the user measured by a weight sensor 401 is displayed on a weight value display section 402. A control section 403 radio-transmits the number assigned to the user selection button which has been pressed along with resultant measurement data and the time and date of measurement from a radio transmitter 404. Upon receipt of the data, the television receiver 10 identifies the user based on the number. Measurement data of each user are stored in association of dates and times when measurement is conducted using the physical measurement apparatus 20. Thus, measurement data of a plurality of users can be managed.

When a user conducts measurement, after pressing a wrong button, the press on the wrong button can be detected at the television receiver upon receipt of measurement data because the measurement data are significantly different from measurement data of the same user stored in the past. In such a case, a notice indicating that a wrong button has been pressed (or prompting the user to conduct measurement again after pressing the right button) may be displayed over the program that is presently watched on the screen.

Another method for managing measurement data of a plurality of users at the television receiver 10 is the use of a face recognition technique. When the television receiver 10 receives measurement data from the physical measurement apparatus 20, users conducting measurement using the physical measurement apparatus 20 may be identified by the face recognition technique, and measurement data of each user may be stored in association with the date and time of measurement. Thus, measurement data of a plurality of users can be managed. When face recognition is performed, a message specific to each of recognized users may be displayed.

The scale is an example of the physical measurement apparatus 20, and the information processing system shown in FIG. 10 or 11 may employ various types of physical measurement apparatus such as a blood pressure monitor and a passometer which are used such that daily measurement values can be recorded. Let us assume that the system includes not only a scale but also a passometer, a blood pressure monitor, and the like and that plural types of measurement data are managed by one television receiver 10. Then, management must be carried out such that the number assigned to each item of data of each physical measurement apparatus is associated with a person. Since the physical measurement apparatus and the television receiver 10 are to communicate with each other on a wireless basis, pairing must be carried out to enable the communication. The physical measurement apparatus may transmit information on themselves to the television receiver to allow the types of the physical measurement apparatus to be registered at the television receiver 10. Based on the registration, a scheme employing a table may be adopted, the scheme involving the step of inputting a number assigned to each user in association with each physical measurement apparatus (see the table shown below) to allow. According to the scheme, relationships between users and physical measurement apparatus can be registered in advance to allow the pieces of data to be managed in association with each other. When a notice or alarm sound is used to prompt users to measurement, each user can be advised of the item to be measured (the apparatus to be used). A different time for measurement can be set for each physical measurement apparatus. A time at which each user is to conduct measurement may be registered in association with each physical measurement apparatus. Each item to be set on the table is input using a GUI provided on the television receiver 10 or running a script downloaded through the internee using a browser.

for conducting measurement using the physical measurement apparatus, an on-screen message prompting the user to conduct weight measurement or the like is displayed over the program presently watched o the screen of the television receiver 10 as shown in FIG. 2. A time for measurement at which a user is prompted to measurement is a time set in advance by the user or a time at which the user usually conducts measurement. A user may be prompted to measurement by an alarm sound instead of an on-screen message. Thus, a user can be prevented from carelessly neglecting measurement, and daily measurement data obtained without missing days can be displayed in a preferable form such as a graph.

Referring to the method of setting a time for measurement at which a user is prompted to measurement by the television receiver 10, it will be convenient if a method for setting such a time based on the times of measurement of past measurement data is available in addition to a method in which a time for measurement is directly input by a user. In consideration to possible cases in which measurement is conducted plural times a day, the time of a day may be divided into blocks of time, and an average of the times of measurement of past measurement may be obtained for each block of time. The average time may be set as a time for prompting a user to conduct measurement. A time for measurement is determined for each user individually. In the case wherein measurement data of a plurality of users are managed by setting a time for measurement for each user separately, the calculation of the time for measurement is carried out by each user.

In consideration to the fact that the television receiver 10 is essentially intended for displaying television programs to be watched by users, it may be preferable to display a notice prompting a user to conduct measurement at such timing that disturbance imparted by such a message to a television program being watched will be minimized. Examples of timing at which disturbance to television programs can be suppressed are shown below. Determination may be made at such timing to check whether no measurement data has been transmitted past a calculated time for measurement and, if no measurement data has been transmitted, a notice may be displayed to prompt the user to conduct measurement using the physical measurement apparatus 20.

A notice may be displayed:

(1) immediately after the power supply of the television receiver 10 is turned on;

TABLE

| User | Apparatus | No. | Measurement Time | Apparatus | No. | Measurement Time | Apparatus | No. | Measurement Time |
|------|-----------|-----|------------------|-----------|-----|------------------|-----------|-----|------------------|
| A | Scale 1 | 1 | 18:00 | Passometer 1 | — | — | Blood pressure meter 1 | 1 | 18:00 |
| B | Scale 1 | 2 | 21:00 | Passometer 2 | — | — | Blood pressure meter 1 | 2 | 21:00 |
| C | Scale 1 | 3 | 8:00 | Passometer 3 | — | — | — | — | — |
| D | Scale 1 | 4 | 16:00 | Passometer 4 | — | — | — | — | — |

In order to control one's physical condition properly, it is important to conduct measurement using a physical measurement apparatus every day. However, most users of physical measurement apparatus tend to neglect the measurement sometimes, whereas the users watch television programs substantially every day as if it were a daily routine.

In the information processing system according to the present embodiment, when no measurement data is transmitted from the physical measurement apparatus 20 past a time for measurement, i.e., a time of the day set by a user as a time (2) several minutes before the end of a program being watched (the ending time of the program can be known by accessing the EPG data of the program being watched);

(3) immediately after a channel switching operation performed by a user;

(4) immediately after a person is detected by a human sensor or the like provided in the television receiver 10;

(5) immediately before the time at which the power supply of the television receiver 10 is normally turned off every day;

(6) for several seconds following an operation of turning off the power supply of the television receiver 10; or (7) when a user performs some operation on the television receiver 10 such as an operation of displaying an EPG.

An advice may be given to a user based on measurement data in addition to the operations of prompting the user to conduct measurement and presenting measurement data in the form of a graph, whereby the user is motivated to continue conducting the measurement every day. There are exemplary modes of feedback provided to a user as described below other than prompting the user to conduct measurement and presenting measurement data.

(1) Words pleasing the user may be displayed when the user completes measurement.

(2) A notice prompting the user to conduct measurement may be repeatedly displayed unless the user conducts measurement, and words having a harder tone may be used each time the message is repeated.

(3) A notice may be displayed when an abrupt change in measurement data is observed or when measurement data indicating a possible problem in the health of the user is detected. For example, if the blood pressure is abnormally higher than the normal, the user may be prompted to conduct re-measurement, and a warning message may be displayed when the blood pressure is still high after the re-measurement.

FIGS. 5A to 5F show operational steps executed by the television receiver 10 in the form of a flow chart. For example, the illustrated operational steps may be implemented in the form of predetermined program codes executed by the CPU 119.

Figure 5A:
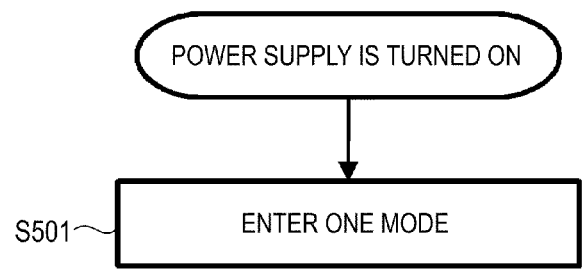
FIG. 5A is a flow chart showing an operational step (turning a power supply on) executed at the television receiver 10.
Figure 5B:
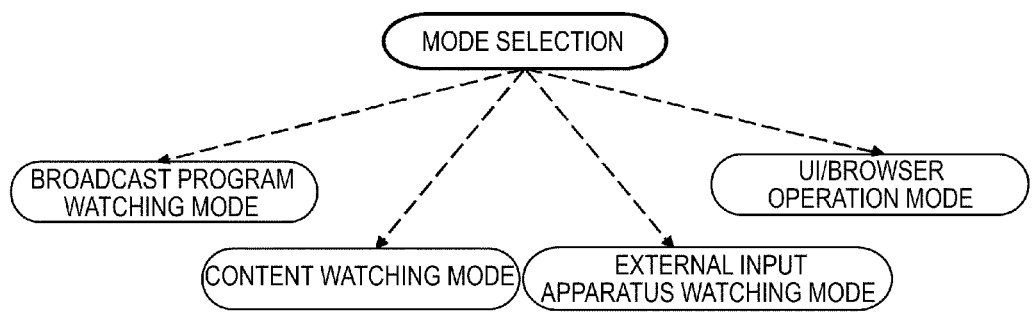
FIG. 5B is a flow chart showing operational steps executed at the television receiver 10 for selecting a mode.

As shown in FIGS. 5A, and 5B, when the power supply of the television receiver 10 is turned on, the receiver enters one of a plurality of modes (step S501). For example, the television receiver may enter the mode in which the receiver had stayed immediately before the power supply was previously turned off. The television receiver may forcibly be put in a broadcast program watching mode. Alternatively, the television receiver may enter a mode selected by the user after the power supply is turned on. The mode that the television receiver enters depends on the specifications of the product.

Figure 5C:
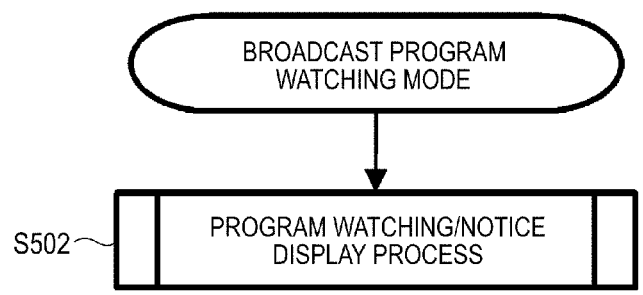
FIG. 5C is a flow chart showing operational steps executed at the television receiver 10 in a broadcast program watching mode.

The "broadcast program watching mode" is a mode to allow a user to watch a broadcast program, and a user can watch a program by selecting a broadcast wave in this mode. As shown in FIG. 5C, when the television receiver is in this mode, a program watching/notice display process, which will be separately defined, is executed (step S502).

A "content watching mode" is a mode for allowing a user to select and watch one of a plurality of content items which can be displayed in advance in the form of a list. Some television receivers have a hard disc recorder incorporated therein which provides the function of recording broadcast programs and accumulating such records. The program content items thus recorded and accumulated may be displayed in the form of a list, and a user may select and watch one item of content. Similarly, a plurality of on-demand content items available on a network may be displayed in the form of a list, and a user may select and watch one item of content.

In the "content watching mode", a display process, which will be separately defined, is executed as shown in FIG. 5D (step S503). The term "display process" in this context means a process of displaying an on-line notice for prompting a user to conduct measurement using a physical measurement apparatus 20, and steps of the process will be detailed later.

Thereafter, a content list, which is a list of the recorded and accumulated program content items, is displayed on a display screen 110 (step S504). When a user selects a desired content item from the content list by operating a remote controller (step S505: Yes), the display process, which will be separately defined, is executed (step S506). Thereafter, a reproduction process is performed on the selected content (step S507).

When the content reproducing process is thereafter terminated or interrupted (step S50$: Yes), the flow returns to step S503.

An "external input watching mode" is a mode for watching and listening to images and sounds from a DVD player (omitted in FIG. 1) which is connected to the television receiver 10 through an input terminal (not shown in FIG. 1) such as an HDMI (High Definition Multimedia Interface).

As shown in FIG. 5E, in the "external input apparatus watching mode", an external input is first displayed (step S509), and the display process, which will be separately defined, is subsequently executed (step S510). Thereafter, the television receiver stands by until another mode is selected (step S511).

A "UI/browser operation mode" is a mode provided to accommodate an EPG display function of the television receiver 10, television operations, display of a dedicated screen for allowing apparatus connected to the television receiver to be operated more easily, and display of data broadcasts. Further, television receivers having a network browser incorporated therein are recently available. The UI/browser operation mode also accommodates operations of such television receivers.

Figure 5F:
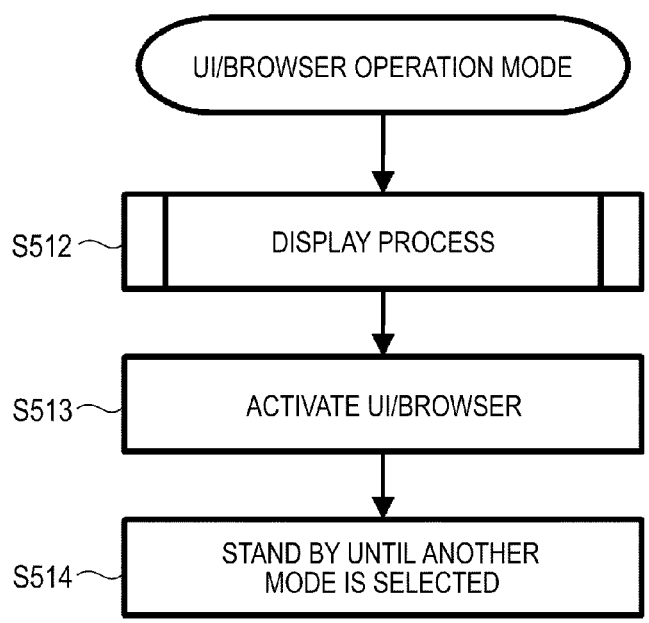
FIG. 5F is a flow chart showing operational steps executed at the television receiver 10 in UI/browser operation mode.

As shown in FIG. 5F, in the "UI/browser operation mode", a display process, which will be separately defined, is performed (step S512), and a UI screen or a browser is subsequently activated (step S513). Thereafter, the television receiver stands by until another mode is selected (step S514).

Although four modes are illustrated in FIGS. 5A to 5F by way of example, each of the modes may be subdivided as occasion demands. For example, the "broadcast program watching mode" may be subdivided to accommodate a plurality of broadcast networks such as surface wave broadcast and satellite broadcast. The "content watching mode" may be subdivided into a mode for watching content accumulated in the hard disc and a mode for watching on-demand content available on a network. The "external input apparatus watching mode" may be subdivided into modes each of which is associated with one input terminal The "UI/browser operation mode" may be subdivided to accommodate each type of user interface, and this mode may alternatively be separated to establish an independent mode for accommodating a browser.

The flow of each mode enters an endless loop when the television receiver stands by until another mode is selected. Any process in the flow of each mode is interrupted when another mode is selected, and the processes of the selected mode are performed from the beginning of the flow.

Figure 6:
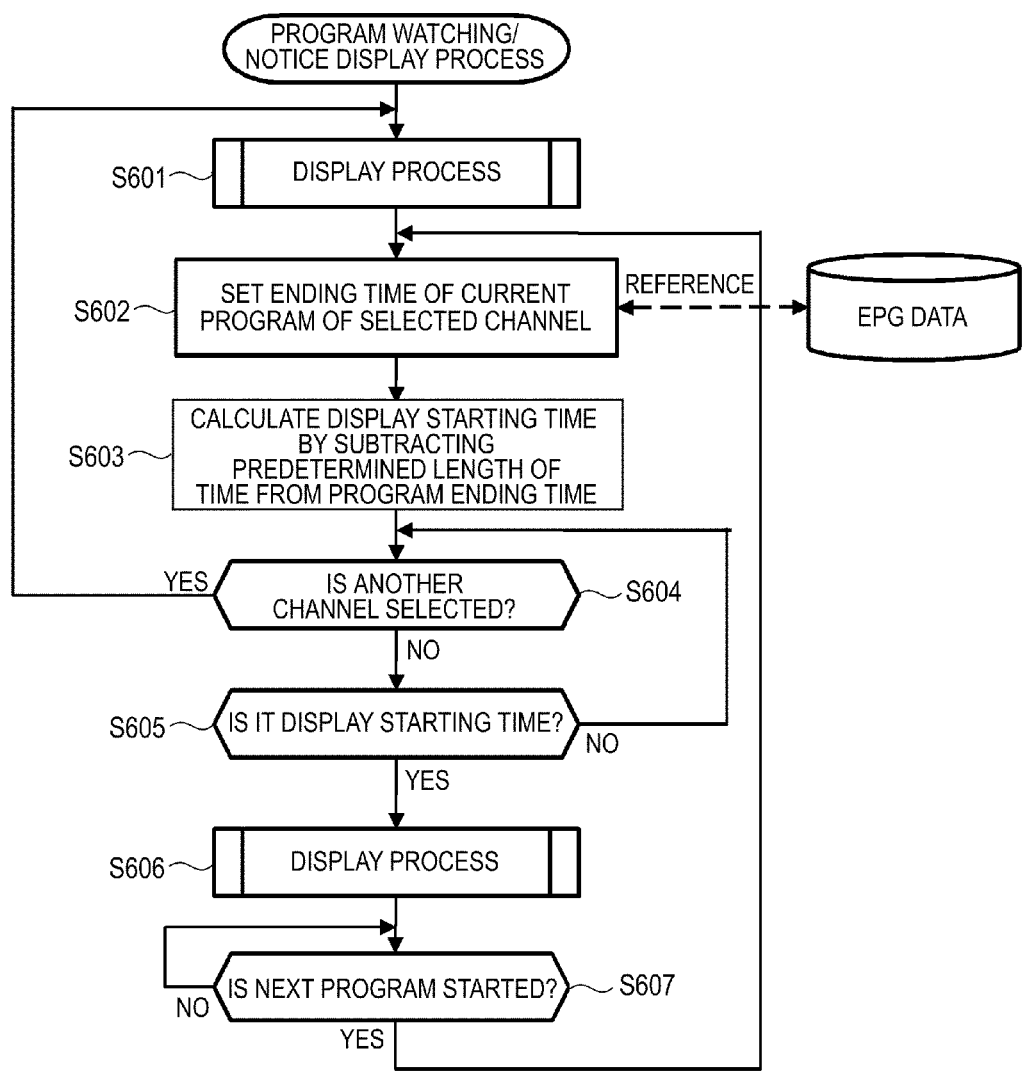
FIG. 6 is a flow chart showing processing steps of a program watching/notice display process (step S502) executed in the "broadcast program watching mode" in detail.

FIG. 6 shows processing steps of the program watching/notice display process (step S502) executed in the "broadcast program watching mode" in detail in the form of a flow chart. For example, the processing steps can be implemented in the form of predetermined program codes executed by the CPU 119.

In the "broadcast program watching mode", a display process, which will be separately defined, is first performed (step S601).

Next, information on the program being watched is acquired from EPG data based on the channel being watched and the current time, and the ending time of the program is extracted from the information (step S602). The EPG data are data of program lists of all channels transmitted to the television receiver as data broadcast signals using digital broadcast, and the data are acquired in advance and accumulated in the television receiver 10 for displaying program lists.

In order to display a notice for prompting the user to conduct measurement at a time immediately preceding the end of the program, a time calculated by subtracting a predetermined length of time from the program ending time is set as a display starting time (step S603).

Thereafter, the television set stands by until the display starting time comes (step S605: No). When the user performs a tuning operation before the display starting time (step S604: Yes), the flow returns to step S601 at which a display starting time associated with the program broadcast over the newly selected channel is set.

When the display starting time comes (step S605: yes), a display process, which will be separately defied, is performed (step S606). After the display process, the television receiver stands by until the program ends. When the next program is started (step S607: Yes), the flow returns to step S601 to set the next display starting time.

The steps of the program watching/notice display process shown in FIG. 6 constitute a flow of processes for prompting a user to conduct measurement when the television receiver enters the "broadcast program watching mode", when a channel is switched to another, or when the end of a program is coming soon.

Figure 7:
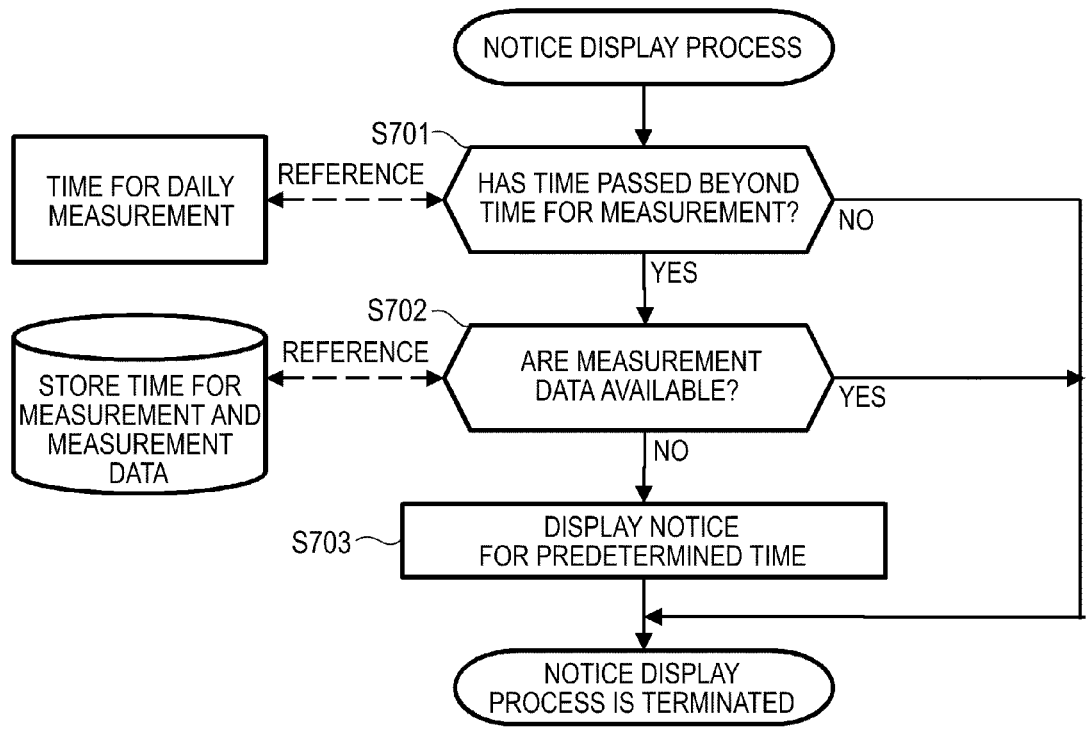
FIG. 7 is a flow chart showing steps of a process of displaying a notice prompting a user to conduct measurement.

FIG. 7 is a flow chart detailing the steps of the process of displaying a notice for prompting a user to conduct measurement executed at steps S503, S507, S510, and S512 of the flow chart shown in FIG. 5F and the steps S601 and S606 of the flow chart shown in FIG. 6. The processing steps are called when conditions for displaying a notice are met in each mode. For example, the steps may be implemented in the form of predetermined program codes executed by the CPU 119.

First, a time for measurement determined in advance is compared with the current time (step S701). When time has not passed beyond the time for measurement yet (step S701: No), the flow of processing steps is terminated.

When time has passed beyond the time for measurement (step S701: Yes), it is checked whether measurement data have already been received from the physical measurement apparatus (step S702). When measurement data have already been received (step S702: Yes), the flow of processing steps is terminated because the user is not required to conduct measurement at this timing.

When the measurement data of interest are not available (step S702: Yes), a notice for prompting the user to conduct measurement is displayed for a predetermined time (step S703).

Recent television receivers include products incorporating a human sensor, and a notice for prompting a user to conduct measurement may be displayed at timing when the user is detected by a human sensor.

Normally, a human sensor provides a detection output so as to save power. Specifically, when it is sensed or determined by such a sensor of a television receiver that a person has left a position in front of the screen, the display is turned off. The display is turned on when the sensor senses or determines that a person has come in front of the screen. Such a sensor section may employ an infrared light sensor which senses infrared light emitted by a person or a camera which senses the face of a person directly. A notice can be displayed as the display is turned on when a person appears in front of the screen regardless of the sensing method employed.

The method of sensing the face of a person using a camera not only allows the faces of a plurality of persons to be sensed simultaneously but also allows a person to be identified from the shape of his or her face. When the shape of the face of each user is registered in advance, a notice can be displayed for a person who is identified as thus described. When another person comes in front of the screen, the new person can be identified, and a notice can be displayed for the person if the user has not conducted measurement.

When a notice is displayed using a human sensor, the operation is performed in an independent manner which is not associated with the mode of the television receiver, unlike the processing steps shown in FIGS. 5A to 5F and FIG. 6.

Figure 8:
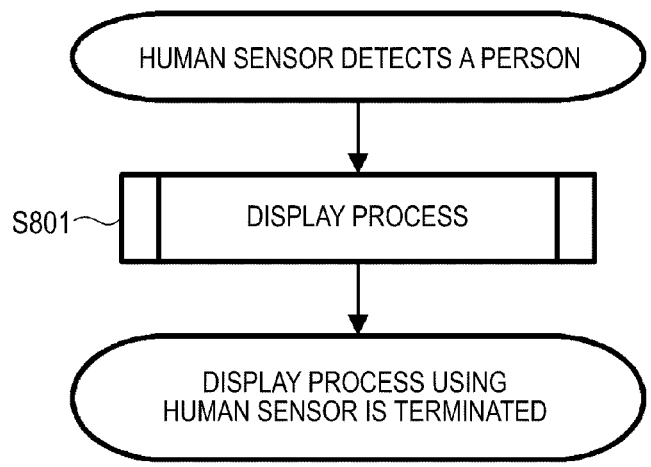
FIG. 8 is a flow chart showing steps of a process of displaying a notice using a human sensor (infrared human sensor)

FIG. 8 shows steps of a process of displaying a notice using a human sensor in the form of a flow chart. FIG. 8 shows an example of processing steps utilizing an infrared human sensor. For example, the processing steps may be implemented in the form of predetermined program codes executed by the CPU 119.

The processing steps are called when a person is detected by the infrared human sensor, and the notice display process shown in FIG. 7 is executed (step S801).

Figure 9:
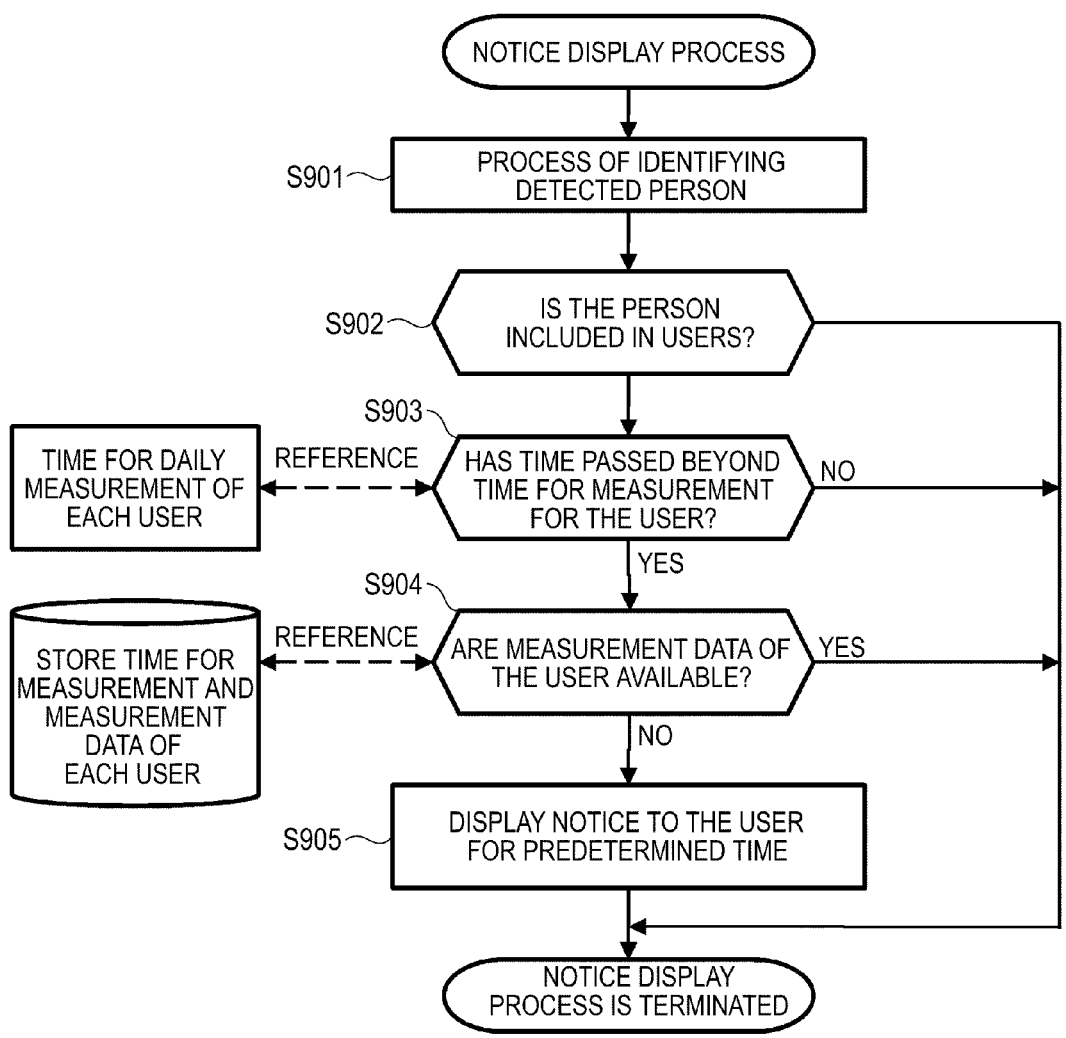
FIG. 9 is a flow chart showing steps of another process of displaying a notice using a human sensor (using a camera as a human sensor)

FIG. 9 shows steps of another process of displaying a notice using a human sensor in the form of a flow chart. FIG. 9 shows an example of processing steps utilizing a camera as a human sensor. For example, the processing steps may be implemented in the form of predetermined program codes executed by the CPU 119.

The processing steps are called when a person is detected by the camera used as a human sensor. First, the detected person is identified based on an image photographed by the camera (step S901). It is checked whether the identified person is a person included in the users of the system (step S902).

When the detected person is not a user of the system (step S902: No), the flow of processing steps is terminated.

When the detected person is a user of the system (step S902: Yes), a time for measurement set for the user in advance is compared with the current time (step S903). When time has not passed beyond the time for measurement (step S903: No), the flow of processing steps is terminated.

When time has passed beyond the time for measurement for the user (step S903: Yes), it is further checked whether measurement data have already been received from the physical measurement apparatus 20 (step S904). When measurement data have already been received (step S904: Yes), the flow of processing step is terminated because the user is not required for conducting measurement at this timing.

When the measurement data of interest are not available (step S904: Yes), a notice for prompting the user to conduct measurement is displayed for a predetermined time (step S905).

The present disclosure has been described with reference to specific embodiments. However, it should be understood by those skilled in the art that various modifications, combinations, sub-combinations and alterations of the embodiments may be made without departing from the spirits of the present disclosure.

The present disclosure has focused on the embodiment in which a television receiver is used as an information processing apparatus for displaying measurement data of a user obtained by a physical measurement apparatus. However, the present disclosure is not limited to such an embodiment. Personal computer and various types of digital apparatus having a display screen may alternatively be used as the information processing apparatus. Physical measurement apparatus which can be used in an information processing system according to the embodiment of the present disclosure include various types of apparatus other than scales, e.g., blood pressure monitors, body composition meters, and passometers.

The present disclosure has been made in the form of exemplification, and the content of the present disclosure should not be construed to be limited to them. The scopes of the appended claims should be taken into consideration to determine the gist of the present disclosure.

What is claimed is:

1. An information processing system comprising:
a physical measurement apparatus measuring the body of a user and radio-transmitting measurement data; and
an information processing apparatus receiving the measurement data radio-transmitted from the physical measurement apparatus, displaying information on the measurement data of the user on a screen, and displaying a notice prompting the user to conduct measurement when no measurement data is received by a predetermined time for measurement,
said information processing apparatus having a human sensor to detect a presence of the user without use of another user, so that the notice prompting the user to conduct the measurement is displayed on the screen when (i) no measurement data is received by the predetermined time for measurement and (ii) the human sensor detects the presence of the user.

2. An information processing apparatus comprising:
a display section;
a human sensor to detect a presence of the user without use of another user;
a radio communication section; and
a storage section,
the radio communication section receiving measurement data of the user radio-transmitted from a physical measurement apparatus, the display section displaying information on the measurement data from the user, a notice prompting the user to conduct measurement being displayed when (i) no measurement data is received by a predetermined time for measurement and (ii) the human sensor detects the presence of the user.

3. An information processing apparatus according to claim 2, further comprising an audio output section to provide audio output of an alarm sound prompting the user to conduct measurement when no measurement data is received by the time for measurement.

4. An information processing apparatus according to claim 2, wherein
measurement data of each user received from the physical measurement apparatus are stored in the storage section in association with a time and date for measurement for each user, and
changes in the measurement data of the user are displayed at the display section in the form of a graph.

5. An information processing apparatus according to claim 4, wherein
the measurement data are transmitted from the physical measurement apparatus, the data being accompanied by identification information of the user, and
a notice is displayed at the display section when the received data are significantly different from past measurement data of the same user which have been stored in the storage section to notify the user of the difference.

6. An information processing apparatus according to claim 2, comprising:
a plurality of physical measurement apparatus, wherein
a separate time for measurement is set for each of the physical measurement apparatus when measurement data of the user are received from the plurality of physical measurement apparatus, and
a process of displaying a notice prompting the user to conduct measurement is performed for each of the physical measurement apparatus.

7. An information processing apparatus according to claim 2, wherein the time for measurement is determined based on the date and time of past measurement data.

8. An information processing apparatus according to claim 2, further comprising:
an antenna;
a tuner circuit for selecting a desired channel from broadcast waves received by the antenna;
a demultiplexer extracting a video signal and an audio signal from a stream transmitted over the selected channel;
a video signal processing circuit processing the video signal; and
an audio processing circuit processing the audio signal; and
an audio output section,
the apparatus displaying the processed video signal at the display section and providing audio output of the processed audio signal from the audio output section.

9. An information processing apparatus according to claim 8, further comprising:
means for recording received content; and
means for reproducing the recorded content.

10. An information processing apparatus according to claim 8, further comprising:
means for inputting content from outside; and
means for reproducing the content input from outside.

11. An information processing system according to claim 1, in which the human sensor has an infrared light sensor which is utilized to detect the presence of the user.

12. An information processing system according to claim 11, in which during operation the infrared light sensor of the human sensor is able to sense infrared light emitted from a face of the user so as to detect the presence of the user.

13. An information processing apparatus according to claim 2, in which the human sensor has an infrared light sensor which is utilized to detect the presence of the user.

14. An information processing apparatus according to claim 13, in which during operation the infrared light sensor of the human sensor is able to sense infrared light emitted from a face of the user so as to detect the presence of the user.

* * * * *